United States Patent
Zarkh et al.

(10) Patent No.: US 8,625,865 B2
(45) Date of Patent: Jan. 7, 2014

(54) METHOD AND APPARATUS FOR NAVIGATING A THERAPEUTIC DEVICE TO A LOCATION

(75) Inventors: Michael Zarkh, Giv'at Shmuel (IL); Amir Blumenfeld, Tel Aviv (IL); Moshe Klaiman, Gadera (IL)

(73) Assignee: Paieon Inc., New York, NY (US)

( * ) Notice: Subject to any disclaimer, the term of this patent is extended or adjusted under 35 U.S.C. 154(b) by 260 days.

(21) Appl. No.: 12/937,717

(22) PCT Filed: Apr. 17, 2008

(86) PCT No.: PCT/IL2008/000526
§ 371 (c)(1),
(2), (4) Date: Oct. 14, 2010

(87) PCT Pub. No.: WO2009/144697
PCT Pub. Date: Dec. 3, 2009

(65) Prior Publication Data
US 2011/0033094 A1    Feb. 10, 2011

(51) Int. Cl.
*G06K 9/00* (2006.01)
(52) U.S. Cl.
USPC .......................................................... 382/128
(58) Field of Classification Search
None
See application file for complete search history.

(56) References Cited

U.S. PATENT DOCUMENTS

| | | | |
|---|---|---|---|
| 7,010,080 B2 | 3/2006 | Mitschke | |
| 2003/0197734 A1* | 10/2003 | Binkert et al. | 345/771 |
| 2005/0107688 A1 | 5/2005 | Strommer | |
| 2005/0182319 A1 | 8/2005 | Glossop | |
| 2008/0095421 A1* | 4/2008 | Sun et al. | 382/131 |

FOREIGN PATENT DOCUMENTS

DE    10 2005 059804    7/2007

OTHER PUBLICATIONS

Michael Zarkh, Moshe Klaiman. "Guide wire navigation and therapeutic device localization for catheterization procedure," International Congress Series, vol. 1281, May 2005, pp. 311-316.*

* cited by examiner

*Primary Examiner* — Nirav G Patel
(74) *Attorney, Agent, or Firm* — Soroker-Agmon (57) ABSTRACT

A method and apparatus for navigating a therapeutic device to a location in a moving organ. A feature is identified in one reference image, such as a calcified spot. Then the target location for the device is determined. If the feature and the target location are not shown on the same frame, registration is performed, and the geometric relation between the feature and the target location is determined. On the positioning stage, the feature is identified in a positioning image, then the target location is indicated on the image. The user then manipulates the device, also visible on the positioning image to the target location. If the feature is not identified automatically in the positioning image, the target location is assumed at the current location, and the feature is marked, which assists the user in identifying the real location of the feature, and manipulating the device to the target location.

19 Claims, 5 Drawing Sheets

METHOD AND APPARATUS FOR NAVIGATING A THERAPEUTIC DEVICE TO A LOCATION

TECHNICAL FIELD

The present disclosure relates to medical imaging in general, and to a method and apparatus for navigating a therapeutic device to a location, in particular.

BACKGROUND

Intravascular device positioning, including navigating the device to its target location and deploying the device at the target location is generally performed under imaging by one of several imaging modalities. A modality commonly used for this purpose is X-ray angiography. The target location for positioning the device is usually seen well when contrast material is injected into the vessel, making the vessels clearly distinguishable. However, each contrast injection exposes the target for only a few seconds, and repeated injections are considered damaging as contrast material is harmful for the kidneys, and excessive radiation is unsafe for the whole body. Moreover, on some procedures and for some kinds of therapeutic devices, the contrast material hides the therapeutic device, making assessment of the device location and thus navigating the device to the required location difficult.

The positioning task is especially difficult for moving organs. For example the heart is subject to its own cyclic motion, breathing, and patient or bed movements. These movements make positioning even more difficult.

Several positioning solutions have been introduced for positioning a device. Some systems, such as International Patent Application published as US2006/0058647, use dedicated equipment based on optical, electromagnetic, or ultrasonic principles for localizing the device. These methods, when applicable, require a complicated calibration procedure. An added modality considerably increases the overall complexity and cost of the procedure. International patent application publication WO 06/103644 discloses a method for registration between an image showing a device using X-Ray and a reference image showing the vessel and the target location, and presenting the device on this reference image. This method is computationally expensive and may provide inaccurate results under conditions of complex motion of the organ. This method is limited since high level of similarity is required between positioning images taken during the therapeutic stage showing the device, and images taken during the reference state showing the organ.

International patent application publication WO 05/020148 discloses a method for overcoming the motion artifact by using data banks containing static vascular maps relating to different phases of the cardiac/respiratory cycles. The positioning image is associated with the corresponding image in the bank by ECG and measured respiration phase. The suggested method requires additional equipment, is not accurate, and does not relate to all the motions, including for example patient movements.

International patent application titled PCT/IL2006/000793 discloses a method for positioning a device in a tubular organ using a guidewire with special markings. Navigation of the device to the target location is carried out using the relation between the markings and the target, the relation extracted by analyzing a reference sequence of images. In addition to the necessity to use a special guidewire, the approach suffers from a number of additional drawbacks. Additional markers on the guidewire make the task of detecting and tracking the device markers much harder. In addition, the method assumes that the guidewire is fixed relatively to the artery throughout the heart motion cycle, which is not always valid. In such cases, shifts of the guidewire inside the vessel introduce inaccuracies.

Thus there is a need in the art for a method for guiding a therapeutic device to an invisible target location in a moving organ. The method should be accurate under typical motions, and reduce the navigation time of the device to the location, as yell as the need for contrast injections.

SUMMARY

A method and apparatus for navigating a therapeutic device to a target location at a target area of a moving organ of a subject. The method and apparatus use a reference image or a reference run in which the target location is determined according to a first feature, and then locate a second feature in a positioning run, upon which the target location or an indication to the location is presented to a user.

In a preferred embodiment of the disclosure there is thus provided a method for navigating a device to a target location in a target area of a moving organ of a subject, the method comprising the steps of: acquiring one or more reference images under a first set of geometric conditions, the reference images showing the target area and one or more first features attached to the moving organ; defining the target location for the device on the reference image; determining a geometric relation between any of the first features and the target location; acquiring one or more positioning images; detecting a second feature in the positioning images; and indicating to a user a discrepancy between the target location and a current location of the device, using the second feature and the geometric relation. Within the method, detecting the second feature optionally comprises the steps of: identifying the second feature in the one of the positioning images and tracking the second feature in one or more second positioning image. Within the method, the positioning images are optionally acquired in geometric conditions substantially similar to the first set of geometric conditions. Within the method, the reference images optionally comprise an X-ray run, wherein one or more images are captured free of contrast material, showing the first feature, and one or more images are captured after injecting contrast material, showing the target area. Within the method, the first feature is optionally an anatomic feature or a deployed device. Within the method, the first feature is optionally a calcification spot. Within the method the geometric relation between any of the first features and the target location is determined by sequential registration of pairs of frames. The method optionally comprises a step of selecting the first set of geometric conditions. Within the method, the moving organ optionally has an elongated shape and the target location is defined as a cross section orthogonal to a main axis of the moving organ. Within the method, the first set of geometric conditions is chosen such that the target location is projected substantially as a line on the reference image or on the positioning image. Within the method, the first set of geometric conditions is optionally determined by acquiring two or more projections, determining two or more two-dimensional directions from the projections, and reconstructing a three-dimensional axis from the two-dimensional directions. Within the method, the geometric relation between the first feature and the target location is optionally a distance between the first feature and the target location. Within the method, the first set of geometric conditions is optionally selected by a user from a plurality of sets. The plurality of sets is optionally presented to the user as a line in a coordinate system of two rotation angles of the imaging device. Within the method, the discrepancy between the target location and a current location of the device is optionally indicated by showing the target location and the current location if the device, or by drawing a feature outline in a location relative to the current location of the device. Within the method, the second feature is optionally detected in a neighborhood of a location of the device. Within the method, detecting the second feature is optionally performed by correlating one or more parts of the positioning image with a template of the first feature. Optionally, correlating the template of the first feature and the second feature is enhanced by integrating a sequence of locally co-registered frames. Within the method, co-registering is optionally performed by tracking a device element, the device element selected from the group consisting of: the device; a pre-deployed device; and an additional device in the vicinity of the second feature. The device element is optionally a device marker or a device corner. Within the method, the additional device is optionally a deflated parked balloon. The method can further comprise a step of selecting a device size based on a three-dimensional distance between two anatomical features measured on two or more projections of the organs. Within the method, the second feature is optionally selected from the group consisting of: the first feature; a feature visible on the positioning image; and the device.

Another aspect of the disclosure relates to a computerized apparatus for navigating a device to a target location within a moving organ of a subject, the apparatus comprising: a communication component for communicating with an imaging device capturing a reference image and a positioning image; a feature identification component for identifying a first feature in the reference image and a second feature in the positioning image; a component for determining geometric relations between two features appearing in one image or in two images; and a component for marking an indication of the first feature on the positioning image.

Yet another aspect of the disclosure relates to a computer readable storage medium containing a set of instructions for a general purpose computer, the set of instructions comprising: acquiring one or more reference images under a first set of geometric conditions, the reference images showing the target area and one or more first features attached to a moving organ; defining the target location for the device on the reference image; determining a geometric relation between the first feature and the target location; acquiring one or more positioning images; detecting a second feature in the positioning images; and indicating to a user a discrepancy between the target location and a current location of the device, using the second feature and the geometric relation.

BRIEF DESCRIPTION OF THE DRAWINGS

Exemplary non-limited embodiments of the disclosed subject matter will be described, with reference to the following description of the embodiments, in conjunction with the figures. The figures are generally not shown to scale and any sizes are only meant to be exemplary and not necessarily limiting. Corresponding or like elements are designated by the same numerals or letters.

DETAILED DESCRIPTION

A method and apparatus for guiding a therapeutic device to a location within a moving organ, the location being externally invisible without imaging equipment. For example, it is sometimes required to position a trans-catheter heart valve (THV) in the aortic annulus which is subject to the heartbeat cycle, breathing and patient moves. In accordance with the disclosure, a diagnostic stage, a reference image or sequence of images is obtained in which the target location and some anatomical or artificial feature attached to the moving organ are observable. The reference sequence is preferably an X-ray run, i.e., an X-ray sequence of images showing the aortic annulus. One or more frames of the run are captured without contrast agent, thus showing distinguishable objects such as artificial devices or calcified areas. Other frames are captured after contrast material is injected, thus showing the aorta, and there may also be intermediates frames showing the organ and the distinguishable objects, but less clearly. Alternatively, a single source such as a Computerized Tomography (CT) scan may show the organ as well as the distinguishable object. Using one of the frames captured with contrast material, the target location for positioning a device is designated, manually or automatically. For example, the line of "hinge-to-hinge" connection of the annulus is designated for a THV. The system detects a calcium spot or another distinguishable object on one of the frames captured without contrast material. Then sequential registration is performed between pairs of frames, optionally using further intermediate frames. Once the images are registered, a combined image showing the distinguishable object and the designated location for the device is generated, and the geometric relation, i.e., the distance vector between the designated location and the distinguishable object can be determined. Since the designated location and the distinguishable object are attached to the organ, such as the aorta, the distance vector is constant regardless of motions of various types.

On a therapeutic stage following the diagnostic stage, the device such as the THV is inserted and navigated, usually using a guidewire, to the designated location. During the therapeutic stage, additional images are captured, preferably without contrast material, showing the distinguishable object. The object is identified, and knowing the distance and direction between the object and the designated location, the location is marked on the image, thus enabling the physician to navigate the device.

The distinguishable object can be a calcified area or another distinguishable anatomic object, but also an artificial object, such as a previously deployed therapeutic device. In such cases, the target location for the second device can be established either as detailed above, or without injecting contrast material, at the known distance and direction from the first device. On the therapeutic stage of placing the second device (balloon, stent and the like) the first device is detected and the target location for the second device is indicated relatively to the location of the previously deployed device.

In case the organ is tubular or elongated, then in order for the images captured during the therapeutic stage to be useful, they should be captured from an angle perpendicular to the organ, so that the distinguishable object as well as the target location can be shown. In order to determine the three-dimensional direction of the organ, two or more two-dimensional images are captured from different perspectives. The direction of the organ is determined using the known geometry of the imaging device, and identifying the organ and its direction within the two or more images.

The resulting set of views orthogonal to the direction of the organ can then be presented to user as a line in a coordinate system consisting of the two rotation angles of an imaging device (a C-arm), together with the projection angles used for capturing the two or more two-dimensional images. If any of these two projections is acceptable to the user as close enough to being perpendicular to the organ, this projection can he suggested as the capturing angle for the diagnostic stage as well as the therapeutic stage. It will be appreciated that the projection angles used during the diagnostic stage and during the therapeutic stage should be substantially the same. The deviation between the projection angles can not exceed a few degrees in any direction. If none of the two projections is sufficiently close to perpendicularity, the user can select any orthogonal projection, and in particular projections close to any of the two projections.

In order to determine the exact size of the device to be deployed within the organ, a physician can mark two points in each of the two images, such as two hinges of the aortic annulus, and knowing the imaging geometry, the real distance between the hinges in the three-dimensional space, and thus the required valve size can be determined.

The general environment in which the disclosure is used is in an operating room wherein a subject is lying on an operation bed, and an imaging device is capturing images of the patient from different perspectives. The images are transferred to a computing platform which performs operations such as image analysis operations on the images, providing a user such as a physician tools including graphic tools for manipulating the images, and others. In preferred embodiment the computing platform, or another computing platform in communication with the first computing platform is adapted to control the imaging device and determine the capturing perspective utilized by the imaging device. The computing platform can be any general purpose computer, such as a desktop computer, a laptop computer, a mainframe computer, or the like. The computing platform is in communication with a display device, such as a CRT, touch screen or any other display device, which can display the captured images, manipulated images, and interface enabling the user to perform computerized operations. The methods of the disclosure are preferably implemented as sets of interrelated computer instructions, arranged as software units such as executables, static libraries, dynamic libraries or other components. Alternatively, the methods or parts thereof can be implemented as firmware ported for a specific processor such as digital signal processor (DSP) or microcontrollers, or can be implemented as hardware or configurable hardware such as field programmable gate array (FPGA) or application specific integrated circuit (ASIC).

Figure 1A:
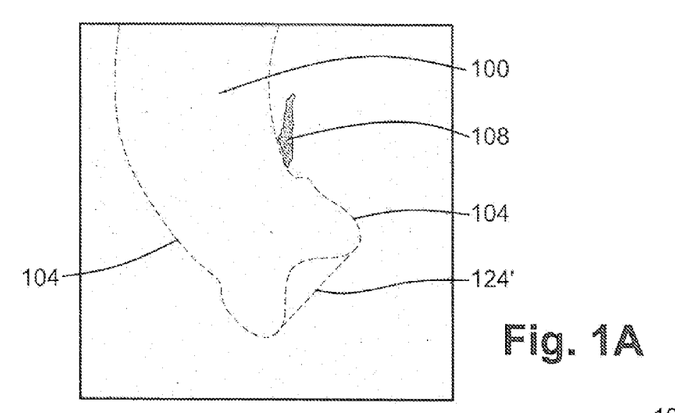
FIG. 1 is a schematic illustration of a set of reference images used during the diagnostic phase, in accordance with a preferred embodiment of the disclosure.
Figure 1B:
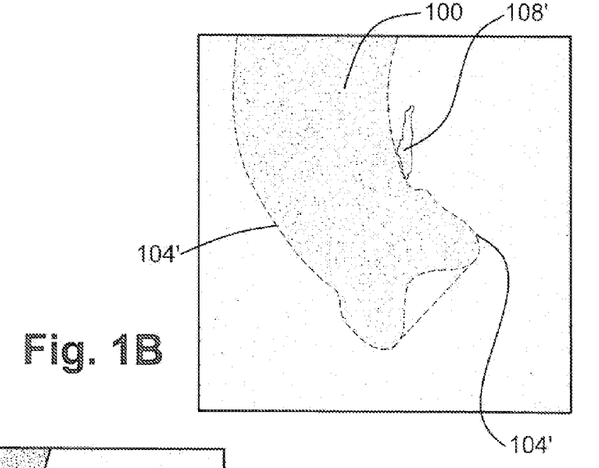
Figure 1C:
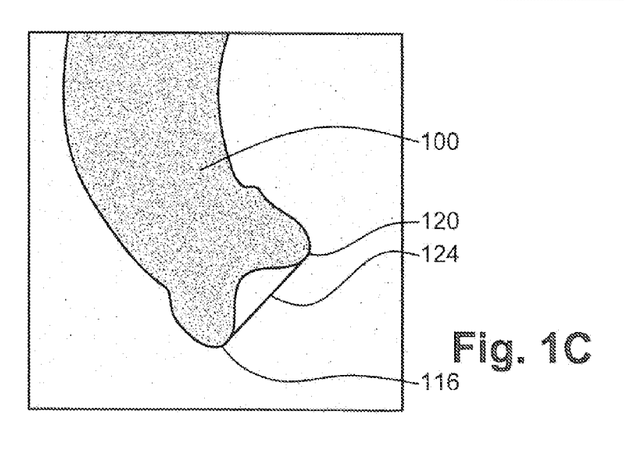

Referring now to FIGS. 1A, 1B, and 1C, showing schematic illustrations of an exemplary set of reference images captured during the diagnostic phase, and markings thereof FIGS. 1A, 1B, and 1C illustrate exemplary images selected from a reference run, i.e., a series of images taken during a short time interval typically between about 4 and about 10 seconds. The reference run preferably comprises between about 10 and about 200 frames, and preferably contains frames free of contrast material taken at the beginning of the run and frames captured with contrast material.

FIG. 1A is an illustration of an X-Ray of aortic area 100, taken without contrast material. Lines 104 illustrate the boundaries of the aorta and leaflets and spot 108 is a calcified spot. Unlike lines 104 which are not seen in X-ray images taken without contrast material, spot 108 is clearly distinguishable.

FIG. 1B is a schematic illustration of an exemplary X-ray image taken with some delay after the injection of contrast material to aortic area 100, after some of the contrast material, but not all of the contrast material has arrived. In FIG. 1B, the boundaries of the aorta and the leaflets, indicated as lines 104' are more distinguishable than in FIG. 1A, but not clearly distinguishable. Calcified spot 108' is less distinguishable than calcified spot 108 of FIG. 1, but is still distinguishable from its surrounding.

FIG. 1C is a schematic illustration of an exemplary X-ray image taken when the aorta is fully opaque due to the contrast material. Lines 104" indicating aorta 100 and the boundaries of the leaflets are clearly seen, but the calcified spot indicated 108 in FIGS. 1 and 108' in FIG. 1B is indistinguishable from its environment. Using FIG. 1C which shows clearly the boundaries of the aorta and two out of the three leaflets, being leaflets 116 and 120, the destination location for a therapeutic device can be determined. For example, a location for a THV can he determined along line 124 connecting leaflet hinges 116 and 120. Then, using image processing techniques such as successive correlation between pairs of neighboring frames, and applying the obtained chain of transformations or shifts, i.e. summing up the shifts between consecutive frames it is possible to register FIG. 1C with FIG. 1A. The registration between FIG. 1C and FIG. 1A enables the marking of line 124' on FIG. 1A, which corresponds to line 124 on FIG. 1C. Indicating line 124' and spot 108 on the same image enables to determine the distance between line 124' and spot 108, i.e. the relative displacement between the designated location of the THV and the calcified spot. It will be appreciated that the frame shown in FIG. 1B, as well as substantially all other frames within the run are used only for registration between a frame showing the target area and the frame showing the calcified spot or another feature. It will be further appreciated that registration is not required if the target location and the calcified spot are shown in the same source, such as a CT scan.

Figure 2A:
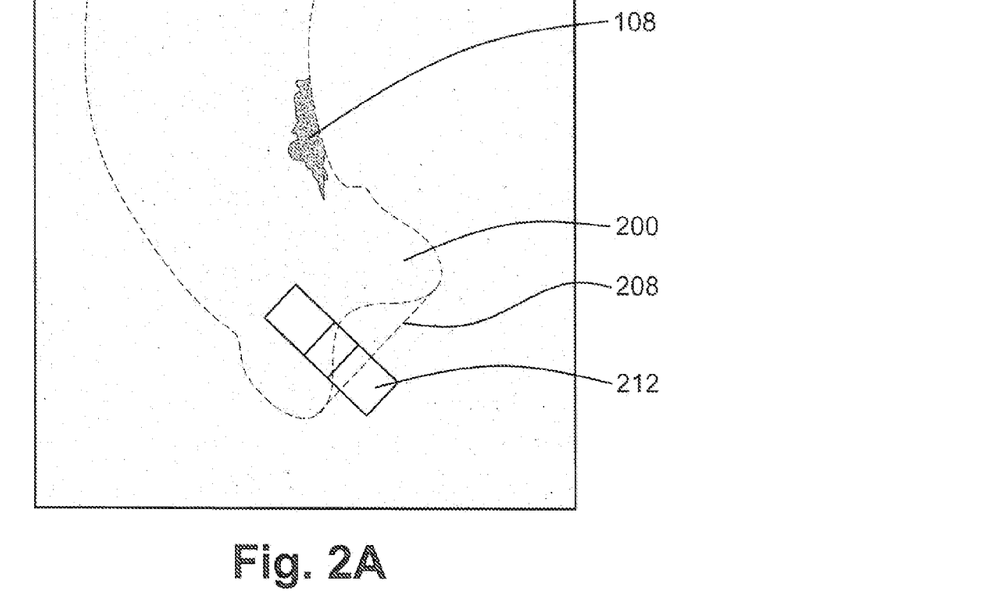
FIG. 2A is a schematic illustration an image used during the therapeutic stage, in accordance with a preferred embodiment of the disclosure.

Referring now to FIG. 2A, showing a schematic illustration of an image shown to a physician during the therapeutic stage, at which the device is to be positioned at its designated location, i.e. navigated to and deployed at the location. FIG. 2A shows an X-Ray image taken during the therapeutic stage, without contrast material injection, with an additional mark 208. FIG. 2A is preferably captured after the device is in the general vicinity of the aortic annulus, so that the aortic annulus and the device can be captured in one image. FIG. 2A shows clearly calcified spot 108, and does not show the aorta and leaflets boundaries 200. Knowing the displacement vector between spot 108 and the designated location for the device, location 208 is marked on the image. FIG. 2A, captured without contrast material, further shows opaque indicators on the device 212. Thus, a physician can navigate device 212 until it is placed exactly on the designated location. For example, the designated location can relate to the distal or proximal end of the device, or to a particular ratio between distal and proximal ends of the device.

Figure 2B:
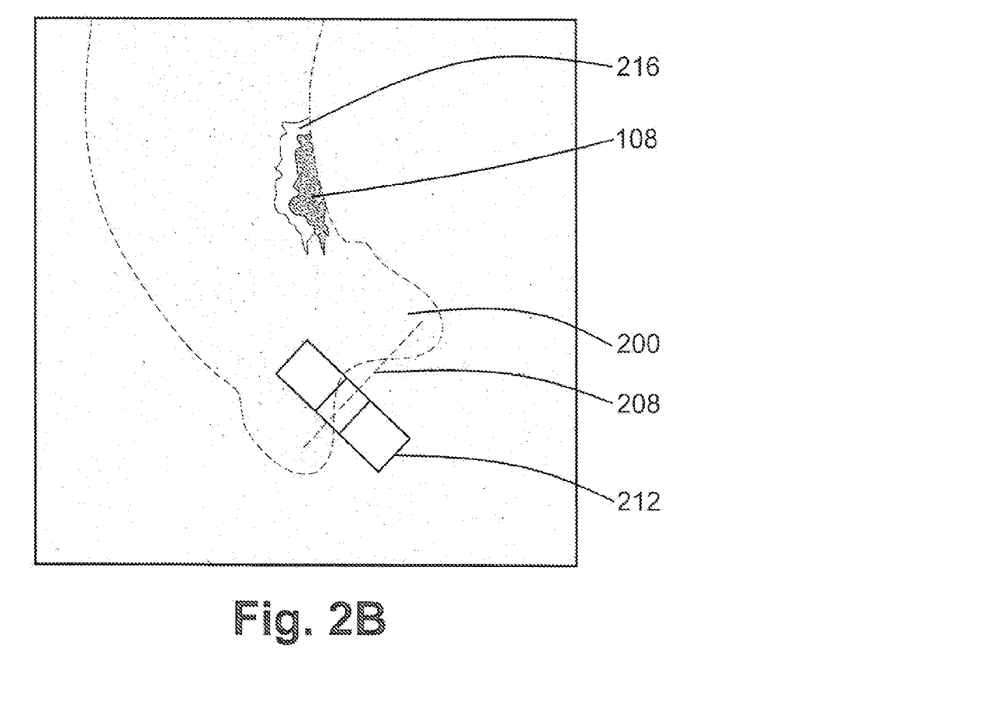
FIG. 2B is a schematic illustration another image used during the therapeutic stage, in accordance with another preferred embodiment of the disclosure.

Referring now to FIG. 2B, showing a schematic illustration of another image shown to a physician during the therapeutic stage, used when spot 108 is seen but can not be identified automatically. Like FIG. 2A, FIG. 2B is also shown when the device is in the vicinity of the designated location. When FIG. 2B is shown, line 208 indicating the designated location is marked at the current position of the device, as if the device is indeed positioned in the designated location. Then boundaries 216 having the shape of the boundaries of spot 108 are marked according to the known distance between the spot and the designated location. Since the image is shown when the device is in the vicinity of the designated location, marked boundaries 216 are in the vicinity of spot 108. Boundaries 216 help the physician focus on the area and identify spot 108 in the image. The physician then positions device 212 so as to make boundaries 216 and spot 108 coincide. When boundaries 216 and spot 108 coincide, device 212 is located on its designated location.

FIGS. 2A or 2B are preferably selected from a run, i.e. a series of images taken during a short time interval, preferably between about 1 second and about 10 seconds, using substantially the same perspective as used when the reference run was captured.

It will be appreciated that instead of an anatomical feature such as a calcified spot, an artificial feature can be used, as long as the feature or object is attached to the organ and is therefore subject to the same movements as the organ. In exemplary embodiments, the feature can be an opaque marker pre-attached to a first device already placed at the location, an opaque marker attached to the first device at the location by parking a deflated balloon used for the first device deployment and inflating a balloon carrying the marker within the first device, an opaque marker attached to the device to he placed which assists the user in focusing on the relevant area, or the like.

Figure 3A:
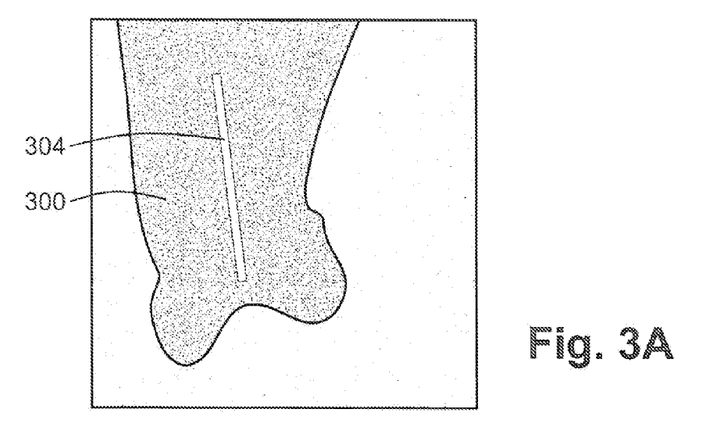
FIGS. 3A and 3B are illustration of images showing the organs during the diagnostic stage.
Figure 3B:
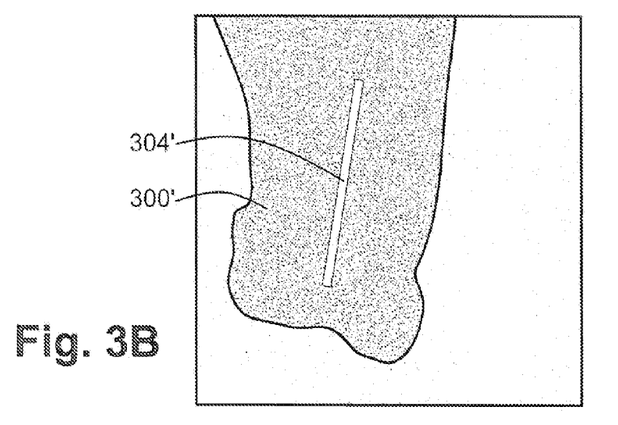
Figure 3C:
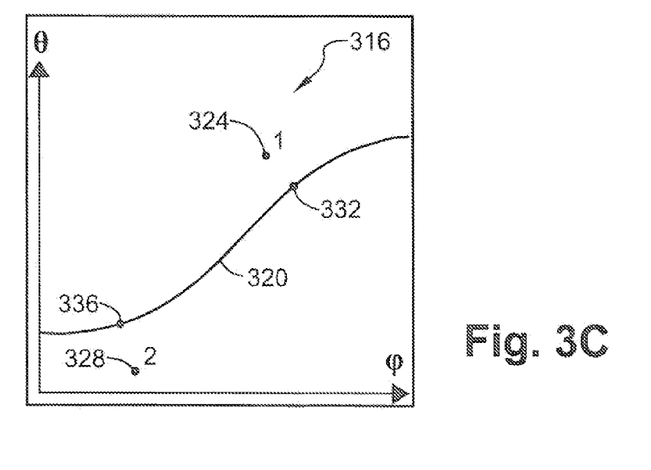
FIG. 3C shows a graphic representation enabling a physician to select an imaging direction, in accordance with a preferred embodiment of the disclosure

Referring now to FIGS. 3A, 3B and 3C, illustrating a method for identifying projection angles to be used by the imaging device during the diagnostic stage and during the therapeutic stage.

Referring now to FIGS. 3A and 3B, showing X-ray images of the aorta and leaflets during the diagnostic stage. FIGS. 3A and 3B are captured using different projection angles. FIG. 3A shows the aorta, referenced 300 and its main axis 304 as captured with contrast material from one perspective, and FIG. 3B shows the aorta, referenced 300' and the main axis 304', as captured from another perspective. Since the projection angles at which FIGS. 3A and 3B were captured are known, the real direction of the main axis can thus be determined. Then, all directions orthogonal to the main axis can be determined as well.

Referring now to FIG. 3C, showing a coordinate system 316 in which each point corresponds to a combination of two rotation angles of the C-arm, and thus to a specific perspective of the X-Ray imaging device. Line 320 comprises of all angle combinations, corresponding to imaging perspectives perpendicular to the main axis of the aorta adjacent to the annulus. Further shown are point 1 (324) and point 2 (328) which corresponds to the angle combinations at which FIG. 3A and FIG. 3B were captured, respectively.

If any of these two projections is acceptable to the user as close enough to being perpendicular to the organ, this projection can be suggested as the capturing angle for the diagnostic stage as well as the therapeutic stage. If none of the two projections is sufficiently close to perpendicularity, the user can select any orthogonal projection, and in particular projections as close as possible to any of the two projections, such as point 332 or point 336.

Figure 4:
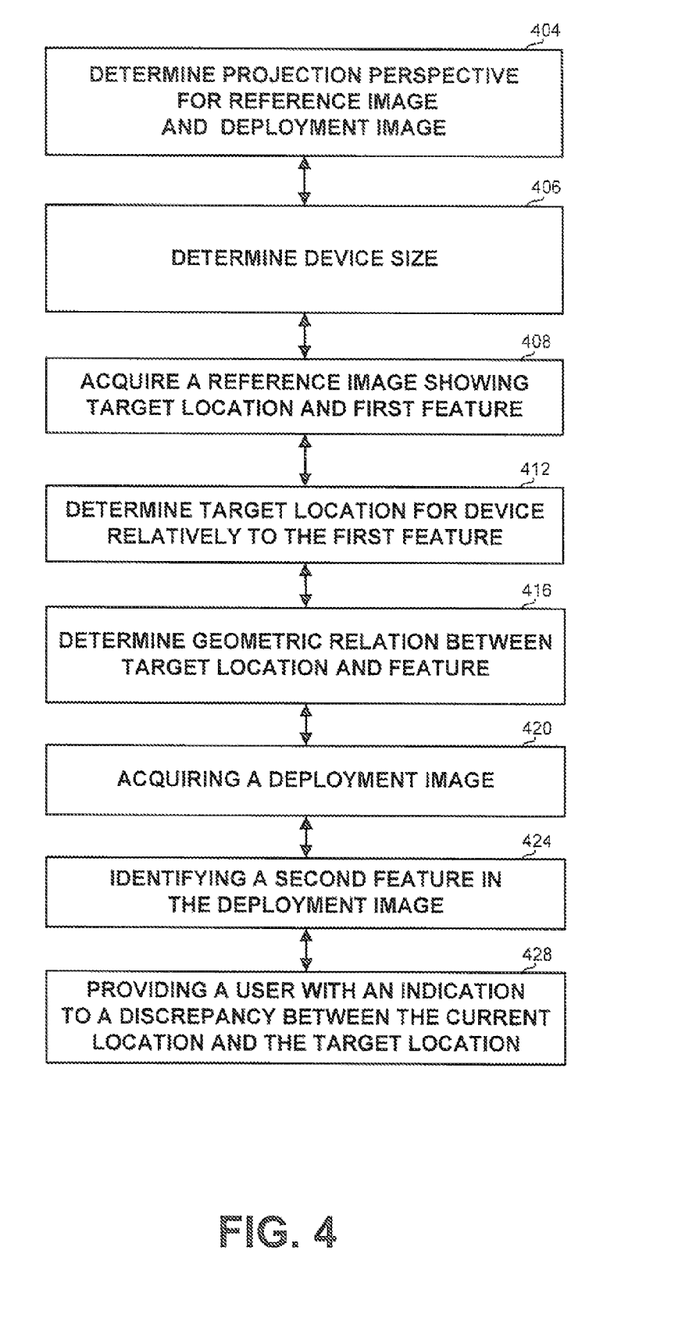
FIG. 4 is a flowchart of the main steps in a preferred embodiment of a method of the disclosure.

Referring now to FIG. 4, showing a flowchart of the main steps in a preferred method for navigating a therapeutic device to a location within or near an organ, the organ being externally invisible.

On optional step 404, a preferred projection perspective for the reference run or reference image and for the positioning image or positioning run is determined, particularly when the relevant organ is tubular or otherwise elongated, and the target location is defined in terms of cross section of the organ. In a preferred embodiment, determining the angle requires the capturing of two images of the organ from two different perspectives. Then the two-dimensional main axis of the organ at the area at which the therapeutic device is to be positioned is determined for each image. Since the capturing perspectives for the two images are known, the three-dimensional direction of the main axis of the organ can be determined from the two two-dimensional directions, for the particular position of the patient. Once the direction of the main axis is determined, all orthogonal directions are known as well, and one of them is preferably chosen so that the captured images show the organ longitudinally, and the target location appears as a line. If a perspective close to perpendicular is selected, then the target location is substantially similar to a line. An angular coordinate system is shown to a user, indicating the capturing perspectives of the two images and a line comprising all directions orthogonal to the organ. The user, such as a physician can choose any point, preferably a point belonging to the line detailed above, associated with a perspective orthogonal to the main axis of the organ. The chosen perspective is preferably used in the reference run during the diagnostic stage, and on the positioning stage.

On optional step 406, the required size or other parameters of the device are determined by the user, for example by marking two points on at least two images, the distance between the points representing the projection of the required size on each of the at least two images, and determining the size using the known geometries of the images. Thus, the device size is selected based on a three-dimensional distance between two anatomical features measured using at least two projections of the organ.

On step 408, one or more reference images are acquired, showing the general area, or the target area of the target location for the device and a first feature attached to the organ. The first feature can be an anatomical feature such as a calcified spot or any other feature visible without injecting contrast material. Alternatively, the feature can be an artificial feature, such as the edge of a device positioned in the general area, a marker attached to such device, a marker attached to a deflated balloon, or the like. The feature can he detected manually by a physician, automatically by the apparatus of the disclosure, or a combination thereof wherein the feature is identified automatically and enhanced manually, or vise versa. If there are multiple reference images, such as images acquired as a reference set, then at least one image from the set should show the organ clearly enough for a user to determine the target location, and at least one image from the set should show the feature.

On step 412, the user, such as a physician determines and marks on the reference image, or on a reference image showing the organ, the target location at which the device is to be positioned.

On step 416, if a single reference image was captured showing the organ and the feature, then the geometric relation between the target location and the feature is determined. If the reference run comprises multiple reference images, then a chain of registrations is performed between pairs of images in the reference run. The registrations are then composed, so as to generate a registration between an image showing the target location and an image showing the feature. Then, the geometric relation between the target location and the feature is determined.

On step 420, which is preferably performed during the therapeutic stage of positioning the therapeutic device, a positioning image or frame, or a positioning run comprising multiple images or frames is acquired. The positioning image shows the general area of the target location and the therapeutic device. Therefore, the positioning image is preferably captured when the therapeutic device is already in the general area of the target location.

On step 424, a second feature is identified in the positioning image, or one or more images of the positioning run. The second feature can be the same as the first feature, such as the calcified spot, or another feature such as the therapeutic device in its current location. The second feature is preferably identified in the neighborhood of the device in its current location device. Step 424 is thus preferably performed when the device is in the general area of the target location, for example between about 0.5 cm away from the target location and about 5 cm away from the target location. If the second feature is the first feature, detecting the first feature is preferably performed by correlating parts of the positioning image with a template of the first feature. Correlating the template of the first feature within an area of the positioning image is optionally enhanced by integrating a sequence of locally co-registered frames of the positioning run. Co-registration of the frames can be performed by using a device element, such as an end or a corner of a device or a marker attached to device. The device may be any device appearing in the positioning image, including the device to be positioned, a previously positioned device or another device such as a deflated parked balloon carrying a marker.

In a preferable embodiment, the detection of the first feature in frames of the positioning run, consists of two phases: identification of the first feature in one of the positioning frames, and tracking the feature in subsequent frames.

Generally, during the identification stage, the template of the first feature is searched for within each relevant sub-area of an area of interest of each positioning frame. The frame at which the template is most likely to be shown is the identified frame. The template is a part of the reference image, the part including the first feature, and a neighborhood of pixels around the first feature. The region of interest is a part of a positioning image adjacent to where the device to be positioned is shown. Both the template and the region of interest are rectangular areas, one dimension of which is parallel to the target line, and the other dimension orthogonal to the first one. Since the appearance of the feature can change periodically in accordance with the heart beat, the template is preferably compared to the region of interest of the positioning image taken at the same phase of the cycle, using ECG. In order to reveal the matched phase without the use of ECG gating or any other external signal, identification may be performed by repeating the correlations of the template as taken from the reference image with regions of interest from sequential frames of the positioning run. Each correlation consists of multiple comparisons between the pixel values in the template, and the pixel value in a sub-area of the area of interest. The highest similarity obtained for the particular frame is the score of the frame. The frame having the highest score among all frames taken throughout a full heart beat cycle is preferably selected as the frame for identification. The identification frame can alternatively be selected as the first frame for which the correlation score exceeds a predetermined value.

Then, during the tracking stage, the template as found in the identified frame is searched for within the next frame. Being found in the next frame the feature in the next frame becomes a template for search in a further following frame, and so on. Since the motion of the device is slow relatively to the anatomical motions, the template is assumed to move insignificantly between two consecutive frames. Therefore, the region of interest at which the template is searched for during the tracking phase can be significantly smaller than the region of interest used during the identification stage.

On step 428, an indication to the discrepancy between the current location of the device and the target location is provided. The indication differs according to the second feature detected on step 424. If the detected feature is the first feature as detected on the reference image or the reference run, such as a calcified spot or a previously positioned device, then the target location can be determined according to the geometric relation determined on step 416, and the target location is then marked on the positioning image. The user then sees the difference between the current location of the device and the target location, and moves the device accordingly.

Another situation is when the second feature is not the feature detected in the reference run or in the reference image. The situation generally occurs when the first feature is not identified in the positioning run. In these cases, it is assumed that the current location of the device is the target location. Then, using the geometric relation between the target location and the first feature, the assumed location of the first feature is marked. Having the assumed mark of the first feature helps the user notice the real location of the first feature. Then, the displacement between the real location of the first feature and the assumed location is the same as the displacement between the real target location and the assumed target location (which is equal to the current location of the device). Thus, moving the device so that the real location of the first feature coincides with the assumed location, will position the device at the real target location.

Figure 5:
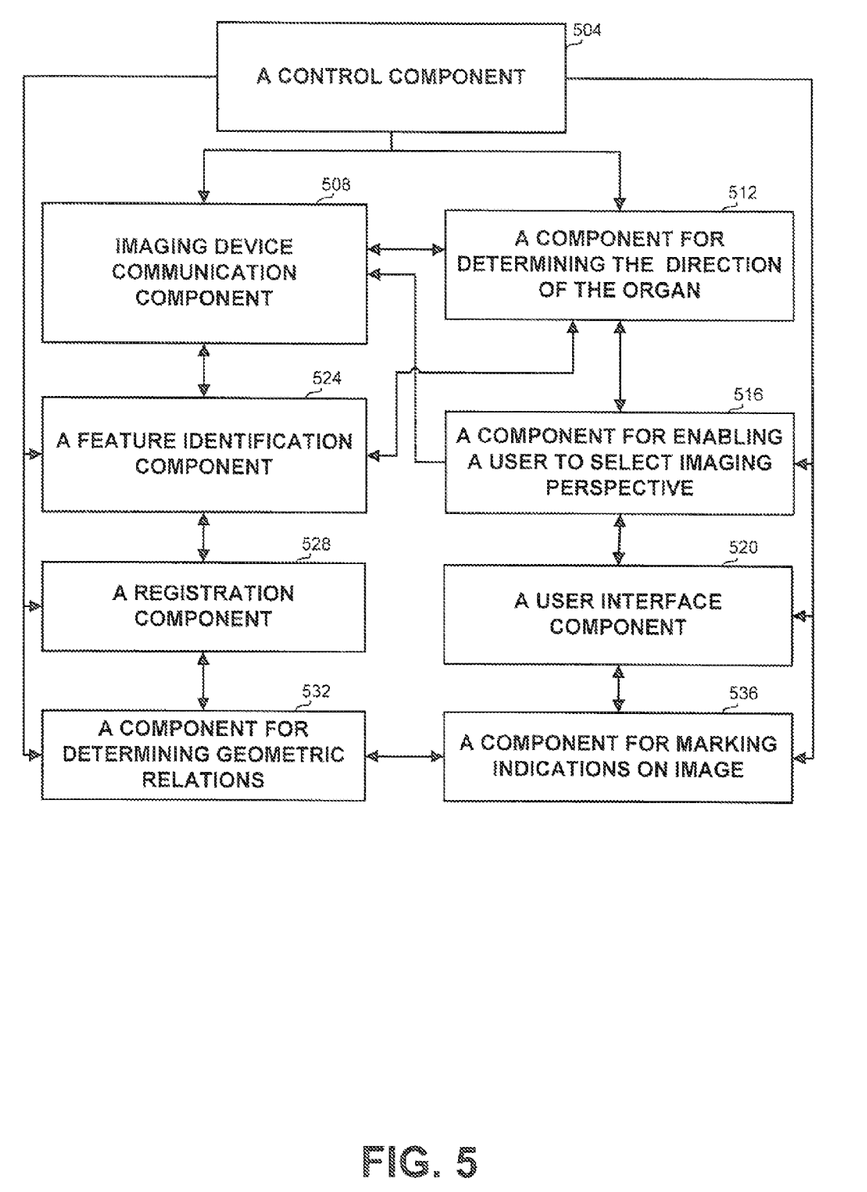
FIG. 5 is a block diagram of the main components in an apparatus for carrying out the method of FIG. 4, in accordance with the disclosure.

Referring now to FIG. 5, showing a block diagram of the main components in an apparatus designed to carry out the disclosed methods. The components are software components executed by a general purpose computer, or firmware ported for a specific processor. The executing computing platform is provisioned with a display device for displaying the images and manipulations thereof, and for enabling the user to make selections when required. The computing platform is in communication with the imaging device, the computing platform receiving captured images from the imaging device and optionally providing instructions such as capturing perspectives to the imaging device. The apparatus comprises control component 504 for controlling the order of activation and data flow between other components. Imaging device communication component 508 is responsible For communication between the apparatus and the imaging device, the communication preferably being two-way, wherein images are received from the imaging device, and control commands relating to the imaging perspective, intensity and other factors are optionally provided to the imaging device. Component 512 is designed to receive two or more images of the organ under discussion, and determine the direction of the organ, if the organ is tubular or elongated. Component 512 is in communication with component 516, designed to enable a user to select, based on the direction of the organ, a preferred imaging perspective. Component 516 is a part of, or in communication with user interface component 520, designed to convey information to, and receive instructions and indications from a user, such as a physician. The apparatus further comprises feature identification component 524 for identifying one or more features in an image, based on image processing techniques, and possibly on data received from a user, such as an indication to the general location of a feature, or the like. Feature identification component 524 provides data to registration component 528, which according to common features detects the similarities between images. Component 528 thus determines the geometric operations which when activated on the coordinate system of one image will yield the coordinate system of the other image. Having the registration parameters between images, component 532 determines the geometric relations between features appearing in different images. Component 536, receiving the geometric locations from component 532, and communicating with user interface component 520 is functional in marking indications on images, for example marking target locations on images showing features attached to the organs, marking the target location on an image showing the current location of a device, and the like.

It will be appreciated by a person skilled in the art that the disclosed methods and apparatus can he used with multiple types of imaging devices taking images of body areas from a point external to the body, such as CT, or MRI. It will also he appreciated that additional embodiments can he designed without deviating from the spirit of the disclosure. For example, other embodiments can be designed for generating relations between Features attached to the organs, or features whose relation to the organ is otherwise known and other features or locations.

It will he appreciated by a person skilled in the art that multiple variations and options can be designed along the guidelines of the disclosed method.

While the disclosure has been described with reference to exemplary embodiments, it will be understood by those skilled in the art that various changes may he made and equivalents may be substituted for elements thereof without departing from the scope of the disclosure. In addition, many modifications may be made to adapt a particular situation, material, step of component to the teachings without departing from the essential scope thereof. Therefore, it is intended that the disclosed subject matter not be limited to the particular embodiment disclosed as the best mode contemplated for carrying out this invention, but only by the claims that follow.

The invention claimed is:

1. A method for navigating a device to a target location in a target area of a moving organ of a subject, the method comprises the steps of:
   acquiring at least one reference image under a first set of geometric conditions, the at least one reference image showing the target area and at least one first feature attached to the moving organ;
   defining the target location for the device on the reference image;
   determining a geometric relation between the at least one first feature and the target location by employing a relative location of said target area and said at least one first feature detected in said reference image;
   acquiring at least one positioning image;
   detecting a second feature in the at least one positioning image,
   indicating to a user a discrepancy between the target location and a current location of the device, using the second feature and the geometric relation, and
   wherein said at least one reference image comprises an X-ray run during which at least one first set of images is captured free of contrast material, showing said at least one first feature, and at least one second set of images is captured after injecting contrast material, showing said target area.

2. The method of claim 1 wherein the positioning image is acquired under geometric conditions similar to the first set of geometric conditions.

3. The method of claim 1 wherein the at least one first feature is an anatomic feature, a calcification spot or a deployed device.

4. The method of claim 1 wherein the geometric relation between the at least one first feature and the target location is determined by sequential registration of pairs of frames.

5. The method of claim 1, wherein the moving organ has an elongated shape and the target location is defined as a cross section orthogonal to a main axis of the moving organ.

6. The method of claim 5 wherein the first set of geometric conditions is chosen such that the target location is projected as a line on the at least one reference image or on the at least one positioning image.

7. The method of claim 6 wherein the first set of geometric conditions is determined by acquiring at least two projections, determining at least two two-dimensional directions from the at least two projections, and reconstructing a three-dimensional axis from the at least two two-dimensional directions.

8. The method of claim 1 wherein the geometric relation between the at least one first feature and the target location is a distance between the at least one first feature and the target location.

9. The method of claim 1 wherein the first set of geometric conditions is selected by a user from a plurality of sets and wherein the plurality of sets is presented to the user as a line in a coordinate system of two rotation angles of the imaging device.

10. The method of claim 1 wherein detecting the second feature comprises the steps of:
   identifying the second feature in the at least one positioning image; and
   tracking the second feature in at least one second positioning image.

11. The method of claim 1 wherein the discrepancy between the target location and a current location of the device is indicated by showing the target location and the current location of the device.

12. The method of claim 1 wherein the discrepancy between the target location and a current location of the device is indicated by drawing a feature outline in a location relative to the current location of the device.

13. The method of claim 1 wherein said detecting the second feature is performed by correlating at least one part of the positioning image with a template of the at least one first feature.

14. The method of claim 13 wherein said correlating the template of the at least one first feature and the second feature is enhanced by integrating a sequence of locally co-registered frames.

15. The method of claim 14 wherein co-registering is performed by tracking a device element, the device element selected from the group consisting of: the device; a pre-deployed deployed device; and an additional device in the vicinity of the second feature.

16. The method of claim 1 further comprising a step of selecting a device size based on a three-dimensional distance between two anatomical features measured using at least two projections of the organ.

17. The method of claim 1 wherein the second feature is selected from the group consisting of: the at least one first feature; a feature visible in the at least one positioning image; and the device.

18. An apparatus for navigating a device to a target location within a moving organ of a subject, the apparatus comprises:
- a communication component for communicating with an imaging device capturing a reference image and a positioning image;
- a feature identification component for identifying a first feature in the reference image and a second feature in the positioning image;
- a component for determining a geometric relation between said first feature appearing in said reference image and a target area appearing in said reference image, and
- a component for marking an indication of the first feature on the positioning image,
- wherein at least one component is executed by a computing platform, and
- wherein said reference image comprises an X-ray run during which a first set of images is captured free of contrast material, showing said first feature and a second set of images is captured after injecting contrast material, showing said target area.

19. A non-transient computer readable storage medium containing a set of instructions for a general purpose computer, the set of instructions comprising:
- acquiring at least one reference image under a first set of geometric conditions, the reference image showing the target area and at least one first feature attached to a moving organ;
- defining the target location for the device on the reference image;
- determining a geometric relation between the first feature and the target location by employing a relative location of said target area and said at least one first feature detected in said reference image;
- acquiring at least one positioning image;
- detecting a second feature in the at least one positioning image; and
- indicating to a user a discrepancy between the target location and a current location of the device, using the second feature and the geometric relation,
- wherein said at least one reference image comprises an X-ray run during which at least one first set of images is captured free of contrast material, showing said at least one first feature, and at least one second set of images is captured after injecting contrast material, showing said target area.

* * * * *